(12) United States Patent
Yamamoto et al.

(10) Patent No.: US 9,346,923 B2
(45) Date of Patent: May 24, 2016

(54) METHOD FOR MANUFACTURING BLOCK COPOLYMER

(75) Inventors: Keiichirou Yamamoto, Tokyo (JP); Masayuki Kitagawa, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/241,924

(22) PCT Filed: Aug. 31, 2012

(86) PCT No.: PCT/JP2012/072160
§ 371 (c)(1),
(2), (4) Date: Apr. 23, 2014

(87) PCT Pub. No.: WO2013/035641
PCT Pub. Date: Mar. 14, 2013

(65) Prior Publication Data
US 2014/0288244 A1    Sep. 25, 2014

(30) Foreign Application Priority Data
Sep. 11, 2011  (JP) .................................. 2011-197760

(51) Int. Cl.
| | | |
|---|---|---|
| C08G 65/333 | (2006.01) | |
| C08G 73/10 | (2006.01) | |
| C08G 81/00 | (2006.01) | |
| C08G 69/10 | (2006.01) | |
| C08G 69/40 | (2006.01) | |
| C08G 73/14 | (2006.01) | |

(52) U.S. Cl.
CPC ............. *C08G 81/00* (2013.01); *C08G 65/333* (2013.01); *C08G 69/10* (2013.01); *C08G 69/40* (2013.01); *C08G 73/14* (2013.01)

(58) Field of Classification Search
None
See application file for complete search history.

(56) References Cited

U.S. PATENT DOCUMENTS

| | | | |
|---|---|---|---|
| 3,979,449 A | 9/1976 | Hirsbrunner et al. | |
| 4,734,512 A | 3/1988 | Kaneko et al. | |
| 4,892,733 A | 1/1990 | Bichon et al. | |
| 5,037,883 A | 8/1991 | Kopecek et al. | |
| 5,182,203 A | 1/1993 | Ebersole et al. | |
| 5,412,072 A | 5/1995 | Sakurai et al. | |
| 5,438,072 A | 8/1995 | Bobee et al. | |
| 5,510,103 A | 4/1996 | Yokoyama et al. | |
| 5,552,517 A | 9/1996 | Martin | |
| 5,571,889 A | 11/1996 | Katoh et al. | |
| 5,614,549 A | 3/1997 | Greenwald et al. | |
| 5,639,832 A | 6/1997 | Kroner et al. | |
| 5,693,751 A | 12/1997 | Sakurai et al. | |
| 5,877,205 A | 3/1999 | Andersson | |
| 5,985,548 A | 11/1999 | Collier et al. | |
| 6,025,385 A | 2/2000 | Shimizu et al. | |
| 6,107,333 A | 8/2000 | Andersson | |
| 6,153,655 A | 11/2000 | Martinez et al. | |
| 6,262,107 B1 | 7/2001 | Li et al. | |
| 6,322,817 B1 | 11/2001 | Maitra et al. | |
| 6,376,470 B1 | 4/2002 | Greenwald et al. | |
| 6,410,731 B2 | 6/2002 | Curran et al. | |
| 6,458,347 B1 | 10/2002 | Sugawara et al. | |
| 6,573,284 B1 | 6/2003 | Riley et al. | |
| 6,596,757 B1 | 7/2003 | Chari et al. | |
| 6,713,454 B1 | 3/2004 | Ekwuribe et al. | |
| 6,720,304 B1 | 4/2004 | Sinn et al. | |
| 6,720,306 B2 | 4/2004 | Greenwald et al. | |
| 6,858,582 B2 | 2/2005 | Yatvin et al. | |
| 7,138,490 B2 | 11/2006 | Nakanishi et al. | |
| 7,176,185 B2 | 2/2007 | Hilfinger et al. | |
| 7,495,099 B2 | 2/2009 | Kitagawa et al. | |
| 7,700,709 B2 | 4/2010 | Masuda et al. | |
| 7,820,759 B2 | 10/2010 | Shimizu et al. | |
| 8,188,222 B2 | 5/2012 | Yamamoto et al. | |
| 8,323,669 B2 | 12/2012 | Kitagawa et al. | |
| 8,334,364 B2 | 12/2012 | Yamamoto et al. | |
| 8,703,878 B2 | 4/2014 | Kitagawa et al. | |
| 8,808,749 B2 | 8/2014 | Kitagawa et al. | |
| 8,920,788 B2 | 12/2014 | Kitagawa et al. | |
| 8,940,332 B2 | 1/2015 | Kitagawa et al. | |
| 9,018,323 B2 | 4/2015 | Yamamoto et al. | |

(Continued)

FOREIGN PATENT DOCUMENTS

| | | |
|---|---|---|
| CA | 2383240 A1 | 3/2001 |
| CA | 2334615 A1 | 8/2001 |

(Continued)

OTHER PUBLICATIONS

Canadian Communication issued Jun. 26, 2013 in co-pending Canadian patent application No. CA 2,664,852.

(Continued)

*Primary Examiner* — Ana Woodward

(74) *Attorney, Agent, or Firm* — Nields, Lemack & Frame, LLC

(57) ABSTRACT

Providing a method for producing a compound represented by formula (1) from a compound represented by formula (2), by which the additive amount of an aryl (C1-C8) alkyl alcohol which may have a substituent and the amount of residual carboxyl groups of pAsp (polyaspartic acid) are controlled.

A production method including obtaining a compound represented by formula (1) by allowing a compound represented by formula (2) to react with an aryl (C1-C8) alkyl alcohol which may have a substituent, and a carbodiimide-based compound in an amount of 2(x+y) equivalents or more relative to the amount of carboxyl groups in formula (2) (sum of x and y), in a solvent at 15° C. to 30° C. for 2 hours to 48 hours, is used.

8 Claims, No Drawings

(56) References Cited

U.S. PATENT DOCUMENTS

| | | | |
|---|---|---|---|
| 9,149,540 | B2 | 10/2015 | Nakanishi et al. |
| 2001/0003779 | A1 | 6/2001 | Curran et al. |
| 2001/0014354 | A1 | 8/2001 | Yokoyama et al. |
| 2001/0041189 | A1 | 11/2001 | Xu |
| 2002/0009426 | A1 | 1/2002 | Greenwald et al. |
| 2002/0016285 | A1 | 2/2002 | Bhatt et al. |
| 2002/0099013 | A1 | 7/2002 | Piccariello et al. |
| 2002/0119951 | A1 | 8/2002 | Seyedi et al. |
| 2002/0161062 | A1 | 10/2002 | Biermann et al. |
| 2002/0183259 | A1 | 12/2002 | Choe et al. |
| 2003/0032593 | A1 | 2/2003 | Wender et al. |
| 2003/0054977 | A1 | 3/2003 | Kumar et al. |
| 2003/0149003 | A1 | 8/2003 | Chaplin et al. |
| 2005/0054026 | A1 | 3/2005 | Atsushi et al. |
| 2005/0119193 | A1 | 6/2005 | Motoyama |
| 2005/0147617 | A1 | 7/2005 | Ji et al. |
| 2005/0171036 | A1 | 8/2005 | Arakawa et al. |
| 2006/0009622 | A1 | 1/2006 | Fuselier et al. |
| 2006/0057219 | A1 | 3/2006 | Nagasaki et al. |
| 2006/0067910 | A1 | 3/2006 | Kitagawa et al. |
| 2006/0099265 | A1 | 5/2006 | Shimizu et al. |
| 2006/0233883 | A1 | 10/2006 | Ishihara et al. |
| 2006/0258569 | A1 | 11/2006 | McTavish |
| 2007/0004674 | A1 | 1/2007 | Shiotsu et al. |
| 2007/0196497 | A1 | 8/2007 | Pouliquen et al. |
| 2008/0113028 | A1 | 5/2008 | Shimizu et al. |
| 2008/0145432 | A1 | 6/2008 | Kakizawa et al. |
| 2008/0221062 | A1 | 9/2008 | Miyamoto et al. |
| 2008/0269218 | A1 | 10/2008 | Kuramochi et al. |
| 2008/0280937 | A1 | 11/2008 | Leamon et al. |
| 2009/0012252 | A1 | 1/2009 | Masuda et al. |
| 2009/0156742 | A1 | 6/2009 | Shimizu et al. |
| 2009/0162313 | A1 | 6/2009 | Kitagawa et al. |
| 2009/0239782 | A1 | 9/2009 | Nakamura et al. |
| 2009/0275732 | A1 | 11/2009 | Hirotsu et al. |
| 2009/0281300 | A1 | 11/2009 | Yamamoto et al. |
| 2010/0004403 | A1 | 1/2010 | Kitagawa et al. |
| 2010/0029849 | A1 | 2/2010 | Yamamoto et al. |
| 2010/0234537 | A1 | 9/2010 | Kitagawa et al. |
| 2010/0292414 | A1 | 11/2010 | Kitagawa et al. |
| 2011/0136990 | A1 | 6/2011 | Harada et al. |
| 2011/0201754 | A1 | 8/2011 | Kitagawa et al. |
| 2011/0294980 | A1 | 12/2011 | Nakanishi et al. |
| 2012/0116051 | A1 | 5/2012 | Kitagawa et al. |
| 2013/0331517 | A1 | 12/2013 | Yamamoto et al. |
| 2014/0024703 | A1 | 1/2014 | Shimizu et al. |
| 2014/0142167 | A1 | 5/2014 | Shimizu et al. |
| 2015/0011715 | A1 | 1/2015 | Nakamura et al. |
| 2015/0259479 | A1 | 9/2015 | Shimizu et al. |

FOREIGN PATENT DOCUMENTS

| | | | |
|---|---|---|---|
| CN | 1307866 A | 8/2001 | |
| CN | 1708540 A | 12/2005 | |
| CN | 1761485 A | 4/2006 | |
| CN | 1800238 A | 7/2006 | |
| CN | 101023119 A | 8/2007 | |
| CN | 101808651 A | 8/2010 | |
| CN | 102037058 A | 4/2011 | |
| EP | 0397307 A2 | 11/1990 | |
| EP | 0583955 A2 | 2/1994 | |
| EP | 0757049 A1 | 2/1997 | |
| EP | 1127570 A2 | 8/2001 | |
| EP | 1489125 A1 | 12/2004 | |
| EP | 1580216 A1 | 9/2005 | |
| EP | 1604687 A1 | 12/2005 | |
| EP | 1792927 A1 | 6/2007 | |
| EP | 1857446 A1 | 11/2007 | |
| EP | 2258397 A1 | 12/2010 | |
| JP | 61-243026 A | 10/1986 | |
| JP | 62-96088 A | 5/1987 | |
| JP | 62-145093 A | 6/1987 | |
| JP | 63-10789 A | 1/1988 | |
| JP | 63-23884 A | 2/1988 | |
| JP | 63-502037 A | 8/1988 | |
| JP | 64-61422 A | 3/1989 | |
| JP | 64-61423 A | 3/1989 | |
| JP | 2-300133 A | 12/1990 | |
| JP | 5-955 A | 1/1993 | |
| JP | 5-117385 A | 5/1993 | |
| JP | 6-107565 A | 4/1994 | |
| JP | 6-206815 A | 7/1994 | |
| JP | 6-206830 A | 7/1994 | |
| JP | 6-206832 A | 7/1994 | |
| JP | 6-329085 A | 11/1994 | |
| JP | 8-48766 A | 2/1996 | |
| JP | 8-503689 H | 4/1996 | |
| JP | 8-507558 A | 8/1996 | |
| JP | 8-310970 A | 11/1996 | |
| JP | 2694923 B2 | 12/1997 | |
| JP | 10-513187 H | 12/1998 | |
| JP | 11-335267 A | 12/1999 | |
| JP | 2000-515132 A | 11/2000 | |
| JP | 2000-516948 A | 12/2000 | |
| JP | 2000-517304 A | 12/2000 | |
| JP | 2001-226294 A | 8/2001 | |
| JP | 2002-69184 A | 3/2002 | |
| JP | 2002-508400 A | 3/2002 | |
| JP | 3268913 B2 | 3/2002 | |
| JP | 2002-512265 A | 4/2002 | |
| JP | 3310000 B2 | 7/2002 | |
| JP | 2003-509385 A | 3/2003 | |
| JP | 2003-509386 A | 3/2003 | |
| JP | 2003-511349 A | 3/2003 | |
| JP | 2003-511423 A | 3/2003 | |
| JP | 2003-524028 A | 8/2003 | |
| JP | 2003-525238 A | 8/2003 | |
| JP | 2003-527443 A | 9/2003 | |
| JP | 2003-342167 A | 12/2003 | |
| JP | 2003-342168 A | 12/2003 | |
| JP | 2003-342269 A | 12/2003 | |
| JP | 2004-530736 A | 10/2004 | |
| JP | 2004-532289 A | 10/2004 | |
| JP | 2005-507912 A | 3/2005 | |
| JP | 2005-508832 A | 4/2005 | |
| JP | 2005-517675 A | 6/2005 | |
| JP | 2005-519122 A | 6/2005 | |
| JP | 2005-533026 A | 11/2005 | |
| JP | 2006-510627 A | 3/2006 | |
| JP | 2006-511571 A | 4/2006 | |
| JP | 2006-517572 A | 7/2006 | |
| JP | 2006-521367 A | 9/2006 | |
| JP | 2006-524673 A | 11/2006 | |
| JP | 2007-511586 A | 5/2007 | |
| JP | 2007-191643 A | 8/2007 | |
| TW | 200812572 A | 3/2008 | |
| WO | 93/24476 A1 | 12/1993 | |
| WO | 96/23794 A1 | 8/1996 | |
| WO | 97/38727 A1 | 10/1997 | |
| WO | 98/02426 A1 | 1/1998 | |
| WO | 98/07713 A1 | 2/1998 | |
| WO | 98/08489 A1 | 3/1998 | |
| WO | 99/30727 A1 | 6/1999 | |
| WO | 99/53951 A1 | 10/1999 | |
| WO | 01/19361 A2 | 3/2001 | |
| WO | 01/19406 A2 | 3/2001 | |
| WO | 01/19407 A2 | 3/2001 | |
| WO | 01/26693 A2 | 4/2001 | |
| WO | 01/64198 A2 | 9/2001 | |
| WO | 01/70275 A2 | 9/2001 | |
| WO | 01/92584 A1 | 12/2001 | |
| WO | 02/06279 A1 | 1/2002 | |
| WO | 02/065986 A2 | 8/2002 | |
| WO | 02/065988 A2 | 8/2002 | |
| WO | 02/066066 A1 | 8/2002 | |
| WO | 03/000771 A | 1/2003 | |
| WO | 03/035008 A2 | 5/2003 | |
| WO | 03/055860 A1 | 7/2003 | |
| WO | 2004/039869 A1 | 5/2004 | |
| WO | 2004/050087 A1 | 6/2004 | |
| WO | 2004/056782 A1 | 7/2004 | |
| WO | 2004/072051 A1 | 8/2004 | |
| WO | 2004/082718 A1 | 9/2004 | |

(56) References Cited

FOREIGN PATENT DOCUMENTS

| WO | 2004/096212 A1 | 11/2004 |
|---|---|---|
| WO | 2005/000300 A1 | 1/2005 |
| WO | 2005/018674 A1 | 3/2005 |
| WO | 2005/066214 A1 | 7/2005 |
| WO | 2006/033296 A1 | 3/2006 |
| WO | 2006/055670 A2 | 5/2006 |
| WO | 2006/055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/116509 A1 | 9/2009 |
| WO | 2009/142326 A1 | 11/2009 |
| WO | 2010/131675 A1 | 11/2010 |

OTHER PUBLICATIONS

International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Office Action mailed Sep. 6, 2013 in co-pending U.S. Appl. No. 12/922,747.
The Merck Index, Fourteenth Edition, 2006, p. 1-16, O'Neil, et al.
Japanese communication, with English translation, mailed Sep. 24, 2013 in co-pending Japanese patent application No. JP 2010-503871.
Office Action mailed Oct. 7, 2013 in co-pending U.S. Appl. No. 10/548,998.
Office Action dated Apr. 17, 2009 in co-pending U.S. Appl. No. 10/548,998.
Office Action dated Jul. 10, 2009 in co-pending U.S. Appl. No. 10/548,998.
Final Rejection dated Mar. 4, 2010 in co-pending U.S. Appl. No. 10/548,998.
Office Action dated Aug. 24, 2010 in co-pending U.S. Appl. No. 11/662,834.
Office Action dated Nov. 12, 2010 in co-pending U.S. Appl. No. 11/662,834.
Final Rejection dated Jun. 8, 2011 in co-pending U.S. Appl. No. 11/662,834.
Office Action mailed Dec. 15, 2011 in co-pending U.S. Appl. No. 11/662,834.
Final Rejection mailed Aug. 21, 2012 in co-pending U.S. Appl. No. 11/662,834.
Office Action dated Sep. 9, 2011 in co-pending U.S. Appl. No. 12/226,962.
Final Rejection mailed Feb. 16, 2012 in co-pending U.S. Appl. No. 12/226,962.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in co-pending U.S. Appl. No. 12/311,086.
Final Rejection dated Jul. 27, 2011 in co-pending U.S. Appl. No. 12/311,086.
Office Action mailed Apr. 18, 2013 in co-pending U.S. Appl. No. 12/311,086.
International Search Report and Written Opinion mailed Jan. 24, 2012 in co-pending PCT application No. PCT/JP2011/076373.
Office Action dated Jan. 21, 2009 in co-pending U.S. Appl. No. 10/548,998.
Office Action—Restriction—mailed Apr. 27, 2012 in co-pending U.S. Appl. No. 12/922,747.
Office Action mailed Jul. 30, 2012 in co-pending U.S. Appl. No. 12/922,747.
Final Rejection mailed Mar. 5, 2013 in co-pending U.S. Appl. No. 12/922,747.
Office Action—Restriction—mailed Jul. 11, 2012 in co-pending U.S. Appl. No. 12/991,041.
Office Action mailed Aug. 22, 2012 in co-pending U.S. Appl. No. 12/991,041.
Final Rejection mailed Mar. 28, 2013 in co-pending U.S. Appl. No. 12/991,041.
Office Action—Restriction—mailed Jan. 29, 2013 in co-pending U.S. Appl. No. 13/319,175.
Office Action mailed Jun. 12, 2013 in co-pending U.S. Appl. No. 13/319,175.
Course for Universities, Third Edition, Revised and supplemented, "Visshaja Shkola" Publishing House, 1981, 656 pages, see p. 265, "High-Molecular Weight Compounds", Shur.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary—11th Edition, 2004, 22 pages.
J. Org. Chem 2001, 66, 8135-8138, "Novel Syntheses of Cis and Trans Isomers of Combretastatin A-4", Gaukroger, et al.
Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview—Amphiphilic Block Copolymers for Drug Delivery", Adams, et al.
Chemistry and Biology, vol. 11, 787-797, Jun. 2004, "Targeting Wide-Range Oncogenic Transformation via PU24FCl, a Specific Inhibitor of Tumor Hsp90", Vilenchik, et al.
Trends in Molecular Medicine, vol. 8, No. 4, (Supp.) 2002, p. S55-61, "Hsp90 Inhibitors as Novel Cancer Chemotherapeutic Agents", Neckers, et al.
Current Cancer Drug Targets, 2003, vol. 3, 385-390, "The Clinical Applications of Heat Shock Protein Inhibitors in Cancer—Present and Future", Banerji, et al.
Cancer Science, Feb. 2004, V. 95, No. 2, 105-111, "Antitumor Activity of Sugar-Modified Cytosine Nucleosides", Matsuda, et al.
Cancer Research vol. 44, Jan. 25-30, 1984, "Antitumor Activity of 1-B-D-Arabinofuranosylcytosine Conjugated with Polyglutamic Acid and its Derivative", Kato, et al.
Journal of Controlled Release vol. 79 (2002), 55-70, "Anticancer Drug Delivery Systems: Multi-Loaded N4-acyl poly (ethylene glycol) prodrugs of ara-C. II. Efficacy in ascites and solid tumors", Choe, et al.
J.of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.
Advanced Drug Delivery Reviews, vol. 20, (1996), 195-201, "Limethason as a lipid microsphere preparation: An Overview", Yokoyama, et al.
Journal of Peptide Science, vol. 3 (1997), 141-144, "Evaluation of Carbodiimides Using a Competition Method", Izdebski, et al.
Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics 2006, vol. 5, 1628-1637, "Preclinical pharmacokinetics and metabolism of a novel diaryl pyrazole resorcinol series of heat shock protein 90 inhibitors", Smith, et al.
Registry Entry for Registry No. 171009-07-07, which entered STN on Dec. 6, 1995, 3 pages.
Registry Entry for Registry No. 7689-03-4, which entered STN on Nov. 16, 1984, 3 pages.

(56) References Cited

OTHER PUBLICATIONS

Merriam Webster Online Dictionary entry for "Derivative", (http://www.merriam-webster.com/dictionary/derivative), last accessed Feb. 9, 2011, 3 pages.
Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000) pp. 607-611, "Methotrexate Esters of Poly(EthyleneOxide)-Block-Poly (2-Hydroxyethyl-L-Aspartamide). Part I: Effects of the Level of Methotrexate Conjugation on the Stability of Micelles and on Drug Release", Li, et al.
Journal of Controlled Release, 2001, V. 74, No. 1-3, pp. 295-302, paragraph of "2. Structure of NK911", "Development of the polymer micelle carrier system for doxorubicin", Nakanishi, et al.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Advanced Drug Delivery Reviews, vol. 55, No. 2, Feb. 2003, pp. 217-250, "Effective drug delivery by PEGylated drug conjugates", Greenwald, et al.
International Search Report dated Dec. 24, 2003 in international patent application No. PCT/JP03/13838 (now U.S. Pat. No. 7,495,099).
Taiwanese Communication dated Nov. 30, 2006 in international patent application No. TW092130275 (now U.S. Pat. No. 7,495,099).
Russian Communication dated Apr. 20, 2007 in international patent application No. RU2005116309 (now U.S. Pat. No. 7,495,099).
European Communication dated Sep. 25, 2008 in international patent application No. EP03769949.3 (now U.S. Pat. No. 7,495,099).
International Search Report dated May 11, 2004 in co-pending international patent application No. PCT/JP2004/003647.
Chinese Communication dated Oct. 20, 2006 in co-pending international patent application No. CN200480007329.5.
Russian Communication dated Jun. 27, 2007 in co-pending international patent application No. RU2005132309/04.
European Communication dated Feb. 17, 2009 in co-pending international patent application No. EP04721673.4.
Chinese Communication, with English translation, dated Apr. 17, 2009 in co-pending international patent application No. CN200480007329.5.
European Communication dated Jun. 5, 2009 in co-pending international patent application No. EP04721673.4.
Korean Communication dated Nov. 8, 2010 in co-pending international patent application No. 10-2005-7017245.
International Search Report dated Nov. 15, 2005 in co-pending international patent application No. PCT/JP2005/017127.
Taiwanese Communication dated Jul. 22, 2011 in co-pending Taiwanese patent application No. 094132581.
European Communication, dated Oct. 28, 2011 in co-pending European Patent Application No. EP 05783310.5.
Taiwanese Communication, with English translation, dated Dec. 14, 2011 in co-pending Taiwanese Application No. 094132581.
International Search Report dated Jul. 25, 2006 in international patent application No. PCT/JP2006/308826 (now U.S. Pat. No. 7,700,709).
International Search Report dated May 15, 2007 in co-pending international patent application No. PCT/JP2007/055809.
International Search Report dated Aug. 21, 2007 in co-pending international patent application No. PCT/JP2007/060026.
European Communication dated Oct. 23, 2009 in co-pending international patent application No. EP07743461.1.
Chinese Communication, with English translation, dated Aug. 11, 2010 in co-pending international patent application No. CN2007800177809.
Russian Communication, with English translation, dated May 16, 2011 in co-pending international patent application No. RU2008149932/04.
Chinese Communication, with English translation, dated Sep. 23, 2011 in co-pending Chinese patent application No. 2007800177809.
Australian Communication, dated Oct. 28, 2011 in co-pending Australian Patent Application No. 2007252678.
International Search Report dated Oct. 16, 2007 in co-pending international patent application No. PCT/JP2007/063990.
Chinese Communication dated Nov. 10, 2010 in co-pending international patent application No. CN 200780027210.8.
International Search Report dated Jan. 8, 2008 in co-pending international patent application No. PCT/JP2007/068841.
Japanese Communication, with English translation, mailed Mar. 26, 2013 in co-pending Japanese Patent Application No. 2008-537500.
International Search Report dated Jan. 29, 2008 in co-pending international patent application No. PCT/JP2007/071532.
European Communication mailed Jan. 27, 2012 in co-pending European Patent Application No. 07831039.8.
International Search Report dated Jan. 29, 2008 in co-pending international patent application No. PCT/JP2007/071305.
International Search Report dated Dec. 9, 2008 in co-pending international patent application No. PCT/JP2008/067413.
Chinese Communication, with English translation, dated Oct. 10, 2011 in co-pending Chinese Patent Application No. 200880109404.7.
Japanese Communication, with partial English translation, mailed May 14, 2013 in co-pending Japanese patent application No. JP 2009-534401.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
European Communication mailed May 24, 2013 in co-pending European patent application No. 09722008.1.
International Search Report, dated Jul. 21, 2009 in co-pending PCT application No. PCT/JP2009/058325.
International Search Report dated Aug. 10, 2010 in co-pending PCT application No. PCT/JP2010/058034.
Chinese Communication, with English translation, mailed Feb. 22, 2013 in co-pending Chinese Patent Application No. 201080021960.6.
Final Rejection mailed Jan. 10, 2014 in co-pending U.S. Appl. No. 13/319,175.
Chinese Communication, with English translation, mailed Dec. 31, 2013 in co-pending Chinese patent application No. CN 200980110087.5.
International Search Report mailed Dec. 4, 2012 in corresponding PCT application No. PCT/JP2012/072160.
Written Opinion mailed Dec. 4, 2012 in corresponding PCT application No. PCT/JP2012/072160.
International Preliminary Report on Patentability mailed Mar. 20, 2014 in corresponding PCT application No. PCT/JP2012/072160.
Final Rejection mailed Apr. 7, 2014 in co-pending U.S. Appl. No. 12/922,747.
Chinese communication, with English translation, mailed Jun. 17, 2014 in co-pending Chinese patent application No. 200980110087.5.
Office Action mailed Aug. 25, 2014 in co-pending U.S. Appl. No. 11/662,834.
Notice of Allowance mailed Sep. 11, 2014 in co-pending U.S. Appl. No. 12/226,962.
Examiner's Answer to Appeal Brief mailed Jul. 29, 2014 in co-pending U.S. Appl. No. 12/311,086.
Notice of Allowance mailed May 15, 2014 in co-pending U.S. Appl. No. 13/319,175.
European communication dated Oct. 29, 2014 in co-pending European patent application No. 09742696.9.
Office Action mailed Nov. 24, 2014 in co-pending U.S. Appl. No. 14/497,703.
Japanese communication, with English translation, mailed Jul. 8, 2014 in co-pending Japanese patent application No. 2010-503871.
Notice of Allowance mailed Oct. 8, 2014 in co-pending U.S. Appl. No. 12/922,747.
English translation of JP 6-206815 (Jul. 26, 1994), "Pharmaceutical Preparation Based on Block Copolymer-Anticancer Drug Complex", by Masayuki Yokoyama, et al., 24 pages, US Patent and Trademark Office, Aug. 2007, Translated by: FLS, Inc.

(56) References Cited

OTHER PUBLICATIONS

Office Action mailed Dec. 31, 2014 in co-pending U.S. Appl. No. 13/971,036.
Notice of Allowance mailed Jan. 28, 2005 in co-pending U.S. Appl. No. 13/884,413.
Final Rejection mailed Mar. 4, 2015 in co-pending U.S. Appl. No. 11/662,834.
European communication dated Mar. 11, 2015 in corresponding European patent application No. 12830758.4.
European communication mailed Apr. 21, 2015 in co-pending European patent application No. 07828587.1.
Chinese communication mailed Apr. 29, 2015 in corresponding Chinese patent application No. 201280043928.7.
Office Action mailed Jul. 7, 2015 in co-pending U.S. Appl. No. 11/662,834.
Final Rejection mailed Jul. 14, 2015 in co-pending U.S. Appl. No. 13/971,036.
Office Action mailed Jun. 22, 2015 in co-pending U.S. Appl. No. 14/727,912.
Final Rejection mailed May 28, 2015 in co-pending U.S. Appl. No. 14/497,703.
Notice of Allowance mailed May 28, 2015 in co-pending U.S. Appl. No. 12/991,041.
Arch. Pharm. (Weinheim), Jan. 1995, vol. 328, No. 10, pp. 737-738, "An Improved and Large Scale Synthesis of the Natural Coumarin Scopoletin", Hauer, et al.
Australian Communication issued May 29, 2015 in corresponding Australian patent application No. 2012305405.
Office action mailed Oct. 5, 2015 in co-pending U.S. Appl. No. 14/108,875.
Matsusaki et al.; "Stably-dispersed and Surface-functional Bionanoparticles Prepared by Self-assembling Amphipathic Polymers of Hydrophilic Poly(y-glutamic acid) Bearing Hydrophobic Amino Acids." 2004, The Chemical Society of Japan; Chemistry Letters, vol. 33, No. 4, pp. 398-399.
Taiwanese communication, with English translation, dated Sep. 10, 2015 in corresponding Taiwanese patent application No. 101133180.
Chinese communication, with English translation, dated Jan. 12, 2016 in corresponding Chinese patent application No. 201280043928.7.
Russian communication, with English translation, dated Jan. 28, 2016 in corresponding Russian patent application No. 2014114264.
Final rejection mailed Apr. 6, 2016 in co-pending U.S. Appl. No. 14/108,875.
Final rejection mailed Jan. 29, 2016 in co-pending U.S. Appl. No. 11/662,834.
Final rejection mailed Jan. 15, 2016 in co-pending U.S. Appl. No. 14/727,912.

METHOD FOR MANUFACTURING BLOCK COPOLYMER

TECHNICAL FIELD

The present invention relates to a micelle preparation containing a block copolymer and a drug using the copolymer, and a method for producing a block copolymer for an anticancer drug containing the micelle composition as an active ingredient.

BACKGROUND ART

Many of drugs, particularly anticancer drugs, are hydrophobic compounds that mostly do not dissolve in water. In order to obtain a desired therapeutic effect using such a drug, usually, the drug is solubilized and administered to a patient. Therefore, solubilization of a sparingly water-soluble drug, particularly a sparingly water-soluble anticancer drug, is important for oral or parenteral preparations, particularly preparations for intravenous administration.

As one of the methods for solubilizing a sparingly water-soluble anticancer drug, a method of adding a surfactant may be used. For example, it is known to use a polyoxyethylene castor oil derivative (Cremophor) for solubilizing paclitaxel. Furthermore, regarding other methods, methods of using a micelle-forming block copolymer as a drug carrier is described in Patent Document 1, Patent Document 2, Patent Document 3, and the like. Patent Document 4, Patent Document 5, and Patent Document 6 describe paclitaxel-encapsulated micelles that use block copolymers having polyethylene glycol (PEG) structural moieties and polyamino acid structural moieties, as drug carriers.

Patent Document 5 describes that paclitaxel-encapsulated micelles having a dominantly high antitumor effect are obtained by altering the structure of the polyamino acid structural moiety of the block copolymer that forms the micelles used in Patent Document 4.

Patent Document 6 describes that when a production method different from that of Patent Document 5 is used, the amount of residual carboxylic acid structures in the structure of the polyamino acid structure moiety of the block copolymer that forms micelles is decreased, and toxicity is decreased as compared with the paclitaxel-encapsulated micelles described in Patent Document 5.

CITATION LIST

Patent Documents

Patent Document 1: JP 6-107565 A
Patent Document 2: JP 6-206815 A
Patent Document 3: JP 11-335267 A
Patent Document 4: JP 2001-226294 A
Patent Document 5: WO 2004/082718 A
Patent Document 6: WO 2006/033296 A

SUMMARY OF INVENTION

Technical Problem

The method for producing a block copolymer described in Patent Document 6 involves first introducing an aryl (C1-C8) alkyl alcohol which may have a substituent, into a PEG-pAsp (polyaspartic acid)-Ac produced by the method described in Patent Document 2, and isolating the product. Thereafter, introduction of a urea transfer residue of pAsp and a cyclization reaction are carried out to reduce the amount of residual carboxyl groups of pAsp. However, the aryl (C1-C8) alkyl alcohol which may have a substituent is partially detached by this heating reaction of the second stage. Accordingly, it has been necessary to carry out the regulation of the introduced ratio of the aryl (C1-C8) alkyl alcohol which may have a substituent in both the first stage and the second stage. Therefore, regulation of the amount of residual carboxyl groups of pAsp and the introduced ratio of the aryl (C1-C8) alkyl alcohol which may have a substituent has been hitherto difficult.

Solution to Problem

The inventors of the present invention conducted a thorough investigation in order to solve the problems described above, and as a result, the inventors surprisingly found a method for producing the block copolymer described in Patent Document 6 in a one-pot process, by applying specifically restricted reaction conditions to the method for producing a block copolymer described in Patent Document 5. Furthermore, the inventors also solve the above-described difficulties in the production, and thus completed the present invention.

That is, the present invention relates to the following:

1) A method for producing a block copolymer represented by the following formula (1):

[Chemical Formula 2]

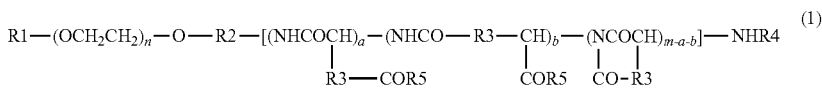

wherein, R1 represents a hydrogen atom or a (C1-C5) alkyl group; R2 represents a (C1-C5) alkylene group; R3 represents a methylene group or an ethylene group; R4 represents a hydrogen atom or a (C1-C4) acyl group; R5 represents a hydroxyl group, an aryl (C1-C8) alkoxy group which may have a substituent, or —N(R6)-CO—NHR7 (wherein, R6 and R7, which may be identical with or different from each other, each represent a (C3-C6) cyclic alkyl group, or a (C1-C5) alkyl group which may be substituted with a tertiary amino group); n represents 20 to 500; m represents 2 to 200; a represents 0 to 100; and b represents 0 to 100, provided the sum of a and b is greater than or equal to 1 and not greater than m; the proportion of R5 representing a hydroxyl group is 0% to 5% of m; the proportion of R5 representing an aryl (C1-C8) alkoxy group which may have a substituent is 10% to 80% of m; and the proportion of R5 representing —N(R6)-CO—NHR7 is 11% to 30% of m, the method including allowing a compound represented by the following formula (2):

[Chemical Formula 1]

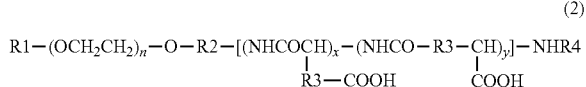
(2)

wherein, R1 represents a hydrogen atom or a (C1-C5) alkyl group; R2 represents a (C1-C5) alkylene group; R3 represents a methylene group or an ethylene group; R4 represents a hydrogen atom or a (C1-C4) acyl group; n represents 20 to 500; x represents 0 to 100; and y represents 0 to 100, provided that the sum of x and y is 2 to 200,
to react with an aryl (C1-C8) alkyl alcohol which may have a substituent, and a carbodiimide-based compound in an amount of 2(x+y) equivalents or more relative to the amount of carboxyl groups in formula (2) (sum of x and y) in a solvent at 15° C. to 30° C. for 2 hours to 48 hours.

2) The method for producing a block copolymer as described in the above item 1), wherein R1 represents a methyl group; R2 represents a trimethylene group; R3 represents a methylene group; R4 represents an acetyl group; n is 80 to 400; m is 15 to 60; a is 5 to 60; and b is 5 to 60.

3) The method for producing a block copolymer as described in the above item 1) or 2), wherein the carbodiimide-based compound is diethylcarbodiimide, diisopropylcarbodiimide, dicyclohexylcarbodiimide, or 1-ethyl-3-(3-dimethylaminopropyl)carbodiimide or an inorganic acid salt thereof.

4) The method for producing a block copolymer as described in any one of the above items 1) to 3), wherein the carbodiimide-based compound is diisopropylcarbodiimide.

Advantageous Effects of Invention

The method for producing a block copolymer of the present invention is such that when the reaction temperature is strictly controlled in the production method described in Patent Document 5, and a reaction is carried out using a carbodiimide-based compound in an amount of 2(x+y) equivalents or more relative to the amount of carboxyl groups in formula (2) (sum of x and y), in contrast to expectation, not the block copolymer described in Patent Document 5 but the block copolymer described in Patent Document 6 is obtained.

The method for producing a block copolymer of the present invention may regulate the rate of introduction of the aryl (C1-C8) alkyl alcohol which may have a substituent into the compound represented by formula (2). This is because the aryl (C1-C8) alkyl alcohol that has been once introduced is not detached by cyclization as in the case of the production method described in Patent Document 6, and the amount of free aryl (C1-C8) alkyl alcohol in the reaction solution does not increase. As a result, the number of unreacted carboxyl groups of pAsp in the compound represented by formula (2) may be reliably decreased. Therefore, as compared with the production method described in Patent Document 6, the method for producing a block copolymer of the present invention is an industrially excellent production method in which production of the product may be easily controlled by a one-stage reaction.

As a result, as compared with the method for producing a block copolymer described in Patent Document 6, the reaction and isolation processes are each carried out once so that the production period may be shortened, and the amount of solvent used may be reduced to about a half the amount of Patent Document 6.

DESCRIPTION OF EMBODIMENTS

The present invention relates to a method for producing a block copolymer represented by the following formula (1) [wherein, R1 represents a hydrogen atom or a (C1-C5) alkyl group; R2 represents a (C1-C5) alkylene group; R3 represents a methylene group or an ethylene group; R4 represents a hydrogen atom or a (C1-C4) acyl group; R5 represents a hydroxyl group, an aryl (C1-C8) alkoxy group which may have a substituent, or —N(R6)-CO—NHR7 (wherein R6 and R7, which may be identical with or different from each other, each represent a (C3-C6) cyclic alkyl group, or a (C1-C5) alkyl group which may be substituted with a tertiary amino group); n represents 20 to 500; m represents 2 to 200; a represents 0 to 100; b represents 0 to 100, provided that the sum of a and b is greater than or equal to 1 and not greater than m; the proportion of R5 representing a hydroxyl group is 0% to 5% of m, the proportion of R5 representing an aryl (C1-C8) alkoxy group which may have a substituent is 10% to 80% of m, and the proportion of R5 representing —N(R6)-CO—NHR7 is 11% to 30% of m], the method including allowing a compound represented by the following formula (2) [wherein, R1 represents a hydrogen atom or a (C1-C5) alkyl group; R2 represents a (C1-C5) alkylene group; R3 represents a methylene group or an ethylene group; R4 represents a hydrogen atom or a (C1-C4) acyl group; n represents 20 to 500; x represents 0 to 100; and y represents 0 to 100, provided that the sum of x and y is 2 to 200; while the various numerical values are average values], which has a polyethylene glycol (PEG) structural moiety and a polyamino acid structural moiety, to react with an aryl (C1-C8) alkyl alcohol which may have a substituent and a carbodiimide-based compound in an amount of 2(x+y) equivalents or more relative to the amount of carboxyl groups in formula (2) (sum of x and y), in a solvent at 15° C. to 30° C., and preferably at 20° C. to 30° C., for 2 hours to 48 hours.

[Chemical Formula 3]

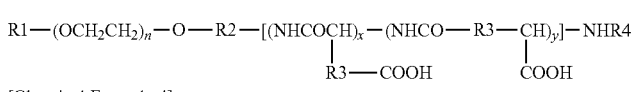
(2)

[Chemical Formula 4]

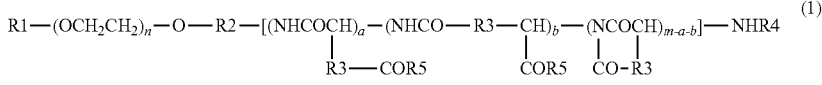
(1)

In regard to the compounds represented by formulas (1) and (2) used in the present invention, R1 may be a hydrogen atom or a (C1-C5) alkyl group, but a (C1-C5) alkyl group is preferred. Specific examples of the (C1-C5) alkyl group may include, but not limited to, a methyl group, an ethyl group, an n-propyl group, an isopropyl group, an n-butyl group, an s-butyl group, a t-butyl group, and an n-pentyl group, but particularly, a methyl group is preferred.

Specific examples of the (C1-C5) alkylene group of R2 may include, but not limited to, a methylene group, an ethylene group, a trimethylene group, and a tetramethylene group, and an ethylene group and a trimethylene group are preferred.

R3 may be a methylene group or an ethylene group, but a methylene group is preferred.

R4 may be a hydrogen atom or a (C1-C4) acyl group, and a (C1-C4) acyl group is preferred. Specific examples may include, but not limited to, a formyl group, an acetyl group, a propionyl group, and a butyroyl group, and an acetyl group is particularly preferred.

In regard to the compound represented by formula (2), n is 20 to 500, and preferably 80 to 400. x is 0 to 100, and preferably 5 to 60. y is 0 to 100, and preferably 5 to 60. The sum of x and y is 2 to 200, preferably 10 to 100, and particularly preferably 5 to 60.

In the compound represented by formula (1), the aryl (C1-C8) alkoxy group for R5 may be a linear or branched (C1-C8) alkoxy group to which an aromatic hydrocarbon group such as a phenyl group or a naphthyl group is bonded. Specific examples may include, but not limited to, a benzyloxy group, a phenethyloxy group, a phenylpropoxy group, a phenylbutoxy group, a phenylpentyloxy group, a phenylhexyloxy group, a phenylheptyloxy group, a phenyloctyloxy group, a naphthylethoxy group, a naphthylpropoxy group, a naphthylbutoxy group, and a naphthylpentyloxy group.

Examples of the substituent for the aryl (C1-C8) alkoxy group which may have a substituent may include, but not limited to, lower alkoxy groups such as a methoxy group, an ethoxy group, an isopropoxy group, an n-butoxy group and a t-butoxy group; halogen atoms such as a fluorine atom, a chlorine atom and a bromine atom; a nitro group; and a cyano group. Substituted forms having a number of substitutions of the substituents of from one to the maximum number capable of substitution at every possible position of substitution are included in the present invention, but an unsubstituted form is preferred.

The aryl (C1-C8) alkoxy group which may have a substituent may be an unsubstituted phenyl (C1-C6) alkoxy group. Examples may include, but not limited to, an unsubstituted benzyloxy group, an unsubstituted phenethyloxy group, an unsubstituted phenylpropoxy group, an unsubstituted phenylbutoxy group, an unsubstituted phenylpentyloxy group, and an unsubstituted phenylhexyloxy group. Preferred examples may include, but not limited to, an unsubstituted benzyloxy group and an unsubstituted phenylbutoxy group.

Specific examples of the (C3-C6) cyclic alkyl group, or the (C1-C5) alkyl group which may be substituted with a tertiary amino group for R6 and R7 may include, but not limited to, a cyclopropyl group, a cyclopentyl group, a cyclohexyl group, a methyl group, an ethyl group, an isopropyl group, an n-butyl group, a 3-dimethylaminopropyl group, and a 5-dimethylaminopentyl group. Among them, an ethyl group, an isopropyl group, a cyclohexyl group, and a 3-dimethylaminopropyl group are preferred, and an isopropyl group is particularly preferred.

In regard to the compound represented by formula (1), n is preferably in the same range as that for the formula (2), and m is 2 to 100, preferably 10 to 100, and particularly preferably 15 to 60. The sum of a and b is greater than or equal to 1 and not greater than m.

m in the formula (1) means the degree of polymerization of the amino acid structural unit of the polyamino acid structural moiety. The polyamino acid structural moiety includes various structural units wherein R5 of the formula (1) represents a hydroxyl group, an aryl (C1-C8) alkoxy group which may have a substituent, or —N(R6)-CO—NHR7, and a structural unit having a cyclic imide structure.

The proportion of R5 in the formula (1) representing a hydroxyl group is 0% to 5%, and preferably 0% to 3%, of m. The proportion of R5 representing an aryl (C1-C8) alkoxy group which may have a substituent is 10% to 80%, and preferably 20% to 80%, of m. The proportion of R5 representing —N(R6)-CO—NHR7 is 11% to 30% of m.

It is especially preferable that the proportion of R5 of the compound represented by formula (1) representing a hydroxyl group be 0% of m. The proportion of R5 representing a hydroxyl group being 0% of m means that all of the carboxyl groups of the polyamino acid structural moiety of the compound represented by formula (2) have been substituted with an aryl (C1-C8) alkoxy group which may have a substituent and/or —N(R6)-CO—NHR7. Meanwhile, the proportion of hydroxyl groups of m may be analyzed by high performance liquid chromatography using an anion exchange column, and the case in which the relevant compound is not retained in the column implies that m is 0%. Furthermore, in the present invention, the proportion of hydroxyl groups of m is analyzed by a potential difference titration method using a base, and when m is 0%, the proportion of hydroxyl groups of m is found to be 0.1 mmol/g or less.

In regard to the polyamino acid structural moiety of the compounds represented by formula (1) and formula (2) used in the present invention, the respective amino acid structural unit moieties may be bonded randomly or may be bonded in a block form.

The aryl (C1-C8) alkyl alcohol which may have a substituent that is used in the present invention is an alcohol corresponding to the aforementioned aryl (C1-C8) alkoxy group which may have a substituent.

For the aryl (C1-C8) alkyl alcohol which may have a substituent, compounds that are commercially available may be used. Furthermore, compounds produced by known organic synthesis methods, and compounds produced by applying known organic reactions may also be used.

Next, the reaction between the compound represented by formula (2) and a carbodiimide-based compound will be explained.

The present reaction is carried out in a solvent, and examples of the solvent used may include, but not limited to, polar solvents such as dimethylformamide (DMF), dimethyl sulfoxide (DMSO), acetonitrile, tetrahydrofuran, and dioxane; and non-polar solvents such as benzene, n-hexane, and diethyl ether. Further examples may include water and mixed solvents thereof, and are not limited to these. The amount of use of the solvent is usually about 1 to 100 times by weight based on the raw material compound.

The carbodiimide-based compound used in the present reaction may be a carbodiimide-based compound having a (C3-C6) cyclic alkyl group or a (C1-C5) alkyl group which may be substituted with a tertiary amino group. Specific examples may include, but not limited to, diethylcarbodiimide, 1-ethyl-3-(3-dimethylaminopropyl)carbodiimide (EDC), 1-ethyl-3-(3-dimethylaminopropyl)carbodiimide hydrochloride (EDC.HCl), dicyclohexylcarbodiimide (DCC), and diisopropylcarbodiimide (DIPCI). Among these, the carbodiimide-based compound is preferably DCC or DIPCI, and particularly preferably DIPCI.

The amount of use of the carbodiimide-based compound in the present reaction is 2 (x+y) equivalents or greater, and more preferably 2(x+y) equivalents to 5(x+y) equivalents, relative to the amount of carboxyl groups in the formula (2) (sum of x and y). When an excess amount of the carbodiimide-based compound is used at a reaction temperature of 15° C. to 30° C., the introduction of a urea transfer residue into the polyamino acid structural moiety of the compound represented by formula (2) and the cyclization reaction can be carried out without causing detachment of the aryl (C1-C8) alkyl alcohol which may have a substituent. The carbodiimide-based compound may be used such that the entire amount may be added at the beginning of the reaction, or divided portions may be appropriately added in the middle of the reaction. Preferably, a reaction for introducing an aryl (C1-C8) alkyl alcohol which may have a substituent, a reaction for introducing a urea transfer residue, and a cyclization reaction are carried out using 2(x+y) equivalents or more of a carbodiimide-based compound, subsequently 0.5(x+y) equivalents or more of a carbodiimide-based compound is added so that all of the carboxyl groups of the polyamino acid structural moiety of the compound represented by formula (1) would react, and thus the reaction for introducing a urea transfer residue and the cyclization reaction are completed.

At the time of the reaction between the compound represented by formula (2) and the carbodiimide-based compound, reaction auxiliaries such as N-hydroxysuccinimide, 1-hydroxybenzotriazole (HOBt), N-hydroxy-5-norbornene-2,3-dicarboxylic acid imide (HOBN), 4-dimethylaminopyridine (DMAP), N,N-diisopropylethylamine, or triethylamine may be incorporated, and among them, DMAP is preferred. When the reaction auxiliaries are used, the amount of use thereof is approximately 0.1(x+y) equivalents to 5 (x+y) equivalents, and preferably approximately 0.2(x+y) equivalents to 2(x+y) equivalents, relative to the amount of carboxyl groups in the formula (2) (sum of x and y).

The amount of use of the aryl (C1-C8) alkyl alcohol used in the present reaction is 0.4 to 1.0 molar equivalents relative to 1 mole of carboxyl groups of the compound represented by formula (2). When the amount of use of the aryl (C1-C8) alkyl alcohol used is regulated according to the average degree of polymerization of the compound represented by formula (2), the amount of the aryl (C1-C8) alkyl alcohol introduced can be regulated.

The reaction temperature is usually 15° C. to 30° C., and it is preferable to carry out the reaction at 20° C. to 30° C., and particularly preferably at 22° C. to 27° C. The reaction time is 2 hours to 48 hours, and preferably 6 hours to 36 hours.

EXAMPLES

Hereinafter, the present invention will be described by way of specific Examples, but the present invention is not intended to be limited to the following examples.

The calculation of the reaction ratio of 4-phenyl-1-butanol (PhBuOH) in the Examples was carried out as follows.

<Calculation of reaction ratio of 4-phenyl-1-butanol>

When the mass of the entire reaction solution before adding of DIPCI is designated as Q1, the mass of the entire reaction solution after adding of DIPCI is designated as Q2, the peak area value obtainable with a sample solution before adding of DIPCI (amount of sampling: P1) and determined by reverse phase HPLC as described below is designated as AS, and the peak area value obtainable with a sample solution after adding of DIPCI (amount of sampling: P2) and determined by reverse phase HPLC as described below is designated as AT, the reaction ratio is expressed by the following formula (using the same measuring flask as that used for the two sample solutions):

PhBuOH reaction ratio (%) = [Chemical Formula 5]

$$\left\{ \frac{1 - AT \times P1 \times Q2}{(AS \times P2 \times Q1)} \right\} \times 100$$

The anion exchange HPLC measurement conditions in the Examples were as follows. Meanwhile, in regard to anion exchange HPLC, if a reactant has carboxyl groups, the reactant is retained in the column.

<Conditions for Anion Exchange HPLC Measurement>

Column: TSKgel DEAE-5PW (manufactured by Tosoh Corp.)

Sample concentration: 5 mg/mL

Injection volume: 20 μL

Column temperature: 40° C.

Mobile phase (A) 20 mM Tris-hydrochloric acid buffer solution (pH 8.0):acetonitrile=80:20

(B) 20 mM Tris-hydrochloric acid buffer solution+1 M aqueous solution of sodium chloride (pH 8.0):acetonitrile=80:20

Flow rate: 1 mL/min

Gradient conditions B % (minutes):10(0), 10(5), 100(40), 10(40.1), stop (50.1)

Detector: Ultraviolet-visible light spectrophotometer detector (detection wavelength: 260 nm)

The reverse phase HPLC measurement conditions in Examples were as follows. In addition, measurement for the reaction ratio of 4-phenyl-1-butanol was also carried out under the same conditions.

<Conditions for Reverse Phase HPLC Measurement>

[HPLC]—Absolute calibration curve method—

Column: InertsilL ODS-3, 5 μm (4.6 mm I.D.×150 mm L)

Injection volume: 20 μL

Column temperature: 40° C.

Mobile phase: 0.1% $H_3PO_4$/($H_2O$:$CH_3CN$=60:40)

Flow rate: 1.0 mL/min

Detector: Ultraviolet-visible light spectrophotometer detector (detection wavelength: 260 nm)

Example 1

Production of Block Copolymer 1

DMF (1132 mL) was added to 65.0 g of PEG (average molecular weight: 12000)-pAsp (polyaspartic acid; average degree of polymerization: 41.6)-Ac (in the formula (2) R1 represents a methyl group, R2 represents a trimethylene group, R3 represents a methylene group, R4 represents an acetyl group, n is about 272, x is about 10.4, and y is about 31.2; hereinafter, abbreviated to PEG-pAsp-Ac-1) produced by the method described in Patent Document 2, the compound was dissolved at 35° C., and DMAP (19.2 g) and 4-phenyl-1-butanol (15.9 g: 0.106 moles; 0.67 molar equivalents relative to 1 mole of carboxyl groups of PEG-pAsp-Ac-1) were added thereto. The portion adhered to the time of adding was added in by washing with DMF (66 mL). After it was confirmed that the compounds were dissolved, the reaction solution was adjusted to 25° C., DIPCI (39.7 g:2(x+y)

equivalents relative to the carboxyl groups of PEG-pAsp-Ac-1=83.2 equivalents) was added, the portion adhered at the time of adding was added in by washing with DMF (60 mL), and the reaction solution was allowed to react for 22 hours at 25° C. In this case, after 20 hours from the initiation of reaction, the reaction ratio of the ester bonds of 4-phenyl-1-butanol became constant. On the other hand, according to an analysis by anion exchange HPLC, the reactants were retained in the column. After 22 hours of the reaction, DIPCI (9.92 g:0.5(x+y) equivalents based on the carboxyl groups of PEG-pAsp-Ac-1=20.8 equivalents) was added, and the reaction was continued. It was checked by an analysis by anion exchange HPLC that the reactants were no longer retained in the column, and after 26 hours from the initiation of reaction, the reaction was terminated. The reaction solution was added dropwise to a mixed solvent of heptane and ethyl acetate, and the mixture was stirred. The mixture was left to stand overnight, and a precipitate thus obtained was collected by filtration and dried under reduced pressure. 76.2 g of crude crystals were obtained.

These crude crystals (75.0 g) were dissolved in DMF (1050 mL), and then cation exchange resin DOWEX 50w8 (248 mL) was added thereto. Furthermore, the portion adhered at the time of adding was added in by washing with DMF (75 mL), and the mixture was stirred for 3 hours. The cation exchange resin DOWEX 50w8 was removed by filtration while washing with ethyl acetate, and then the reaction solution thus obtained was added dropwise to a mixed solvent of heptane and ethyl acetate. The mixture was stirred. The mixture was left to stand overnight, and a precipitate thus obtained was collected by filtration and dried under reduced pressure. 73.5 g of block copolymer 1 was obtained.

Block copolymer 1 (17.60 mg) was dissolved in 1 mL of acetonitrile, and 1 mL of water and 2 mL of a 0.5 N aqueous solution of sodium hydroxide were added thereto. The mixture was stirred for 60 minutes at room temperature to hydrolyze the ester bonds, and then the mixture was neutralized with 1 mL of a 4% aqueous solution of phosphoric acid. The amount of liquid was adjusted to 25 mL with 50% hydrated acetonitrile. 4-Phenyl-1-butanol isolated from the prepared liquid by reverse phase HPLC was quantitatively analyzed. As a result of the analysis, the amount of ester-bonded 4-phenyl-1-butanol was 16.3% (w/w) of PEG-pAsp-Ac-1. The reaction ratio of the ester bonds of 4-phenyl-1-butanol was 82.4%, and the ratio of introduction of 4-phenyl-1-butanol was 55.2% of the carboxyl groups of PEG-pAsp-Ac-1.

This block copolymer 1 was analyzed by anion exchange HPLC under the measurement conditions described below, but any peak that indicated retention in the column was not recognized.

Block copolymer 1 (501.4 mg) was accurately weighed, and 25 mL of ethanol was added thereto to suspend the copolymer. Subsequently, 35 mL of water was added thereto to dissolve the suspension. This block copolymer 1 solution was titrated (potential difference titration method) with a 0.1 mol/L potassium hydroxide liquid, and the number of carboxyl groups per gram of block copolymer 1 was calculated by the following formula. As a result, the number of carboxyl groups was 0.05 mmol/g. As described above, since the number of carboxyl groups in the case where the proportion of carboxyl group was 0% was 0.1 mmol/g or less, block copolymer 1 did not have any residual carboxyl groups.

[Chemical Formula 6]

$$\text{Number of carboxyl groups per gram of block copolymer} = \left[\frac{(\text{Sample titer mL}) -}{(\text{Blank titer mL})}\right] \times 0.1 \times f / \text{sample (g)(mmol/g)}$$

Remark) f: Factor of 0.1 mol/L Potassium Hydroxide Liquid

In order to check the amount of bonding of the urea transfer residue in the block copolymer, the amount of diisopropylurea in the block copolymer was measured. Block copolymer 1 (25.18 mg) was accurately weighed, an internal standard solution was added to accurately make up 1 mL, and this was used as a sample solution. Separately, in a container to which 5 mL of the internal standard solution had been introduced in advance, isopropyl isocyanate was accurately weighed, and the internal standard solution was added thereto to accurately make up 20 mL. 2.5 mL of this liquid was accurately weighed, and the internal standard solution was added thereto to accurately make up 50 mL. This was used as a standard solution. Gas chromatography was carried out with 1 μL of the sample solution and 1 μL of the standard solution under the following conditions, and thus the ratios $Q_T$ and $Q_S$ of the peak area of isopropyl isocyanate relative to the peak area of the internal standard material were respectively determined. The amount of diisopropylurea (% (w/w)) in block copolymer 1 was calculated by the following formula. As a result, the amount was 3.5% (w/w).

[Chemical Formula 7]

$$\text{Amount of diisopropylurea (\%)} = \frac{Q_T}{Q_S} \times \frac{\text{weight of isopropyl isocyanate (g)}}{\text{sample weight (g)}} \times \frac{(100 - \text{sample water content (\%)})}{100} \times \frac{1}{4} \times 1.695$$

Internal standard solution: Acetonitrile solution of ethyl acetate (1→2000)

Test conditions:
Detector: Flame ionization detector
Column: The inner surface of a fused silica tube having an inner diameter of 0.53 mm and a length of 30 m, coated with a polyethylene glycol for gas chromatography at a thickness of 1.0 μm
Column temperature: 50° C. for 8 minutes, and then the temperature was increased up to 200° C. at a rate of 25° C. per minute
Inlet port temperature: Constant temperature near 270° C.
Detector temperature: Constant temperature near 250° C.
Carrier gas: Helium
Flow rate: 3.5 mL/min
Split ratio: 1:50
Area measurement range: 10 minutes Example 2

Production of Block Copolymer 2

DMF (536 mL) was added to 30.0 g of PEG (average molecular weight: 12000)-pAsp (polyaspartic acid; average degree of polymerization: 36.4)-Ac (in the formula (2) R1 represents a methyl group, R2 represents a trimethylene group, R3 represents a methylene group, R4 represents an acetyl group, n is about 272, x is about 9.1, and y is about 27.3; hereinafter, abbreviated to PEG-pAsp-Ac-2) produced by the method described in Patent Document 2, the compound was dissolved at 35° C., and DMAP (8.18 g) and 4-phenyl-1-butanol (7.35 g: 0.049 moles; 0.73 molar equivalents relative to 1 mole of carboxyl groups of PEG-pAsp-Ac-2) were added thereto. The portion adhered at the time of adding was added in by washing with DMF (27 mL). After it was confirmed that the compounds were dissolved, the reaction solution was adjusted to 25° C., DIPCI (16.9 g: 2(x+y) equivalents relative to the carboxyl groups of PEG-pAsp-Ac-2=72.8 equivalents) was added. The portion adhered at the time of adding was added in by washing with DMF (27 mL), and the reaction solution was allowed to react for 22 hours at 25° C. In this case, after 18 hours from the initiation of reaction, the reaction ratio of the ester bonds of 4-phenyl-1-butanol became constant. On the other hand, according to an analysis by anion exchange HPLC, the reactants were retained in the column. After 22 hours of the reaction, DIPCI (4.23 g: 0.5(x+y) equivalents based on the carboxyl groups of PEG-pAsp-Ac-2=18.2 equivalents) was added, and the reaction was continued. It was checked by an analysis by high performance liquid chromatography using an anion exchange column that the reactants were no longer retained in the column, and after 26 hours from the initiation of reaction, the reaction was terminated. The reaction solution was added dropwise to a mixed solvent of heptane and ethyl acetate, and the mixture was stirred. The mixture was left to stand overnight, and a precipitate thus obtained was collected by filtration and dried under reduced pressure. 34.3 g of crude crystals were obtained.

These crude crystals (33.5 g) were dissolved in DMF (469 mL), and then cation exchange resin DOWEX 50w8 (111 mL) was added thereto. Furthermore, the portion adhered at the time of adding was added in by washing with DMF (34 mL), and the mixture was stirred for 3 hours. The cation exchange resin DOWEX 50w8 was removed by filtration while washing with ethyl acetate, and then the reaction solution thus obtained was added dropwise to a mixed solvent of heptane and ethyl acetate. The mixture was stirred. The mixture was left to stand overnight, and a precipitate thus obtained was collected by filtration and dried under reduced pressure. 32.2 g of block copolymer 2 was obtained.

Block copolymer 2 was hydrolyzed by the same method as that used in Example 1 and analyzed by reverse phase HPLC. The amount of ester-bonded 4-phenyl-1-butanol was 15.5% (w/w) of PEG-pAsp-Ac-2. The reaction ratio of the ester bonds of 4-phenyl-1-butanol was 77.3%, and the ratio of introduction of 4-phenyl-1-butanol was 56.4% of the carboxyl groups of PEG-pAsp-Ac-2.

Block copolymer 2 was analyzed by anion exchange HPLC under the same conditions as in Example 1, and any peak that indicated retention in the column was not recognized.

A solution of block copolymer 2 was titrated (potential difference titration method) by the same method as in Example 1 with a 0.1 mol/L potassium hydroxide liquid, and the number of carboxyl groups per gram was 0.05 mmol/g. As described above, since the number of carboxyl groups in the case where the proportion of carboxyl group was 0% was 0.1 mmol/g or less, block copolymer 2 did not have any residual carboxyl groups.

For block copolymer 2, the amount of diisopropylurea in block copolymer 2 was calculated by the same method as in Example 1, and the amount was 3.0% (w/w).

Example 3

Production of Block Copolymer 3

DMF (570 mL) was added to 30.0 g of PEG (average molecular weight: 12000)-pAsp (polyaspartic acid; average degree of polymerization: 46.8)-Ac (in the formula (1) R1 represents a methyl group, R2 represents a trimethylene group, R3 represents a methylene group, R4 represents an acetyl group, n is about 272, x is about 11.7, and y is about 35.1; hereinafter, abbreviated to PEG-pAsp-Ac-3) produced by the method described in Patent Document 2, the compound was dissolved at 35° C., and DMAP (9.68 g) and 4-phenyl-1-butanol (7.29 g: 0.0486 moles; 0.61 molar equivalents relative to 1 mole of carboxyl groups of PEG-pAsp-Ac-3) were added thereto, and the portion adhered at the time of adding was added in by washing with DMF (32 mL). After it was confirmed that the compounds were dissolved, the reaction solution was adjusted to 25° C., DIPCI (20.00 g: 2(x+y) equivalents relative to the carboxyl groups of PEG-pAsp-Ac-3=93.6 equivalents) was added. The portion adhered at the time of adding was added in by washing with DMF (32 mL), and the reaction solution was allowed to react for 22 hours at the same temperature. In this case, after 18 hours from the initiation of reaction, the reaction ratio of the ester bonds of 4-phenyl-1-butanol became constant. On the other hand, according to an analysis by anion exchange HPLC, the reactants were retained in the column. After 22 hours of the reaction, DIPCI (5.0 g: 0.5(x+y) equivalents based on the carboxyl groups of PEG-pAsp-Ac=23.4 equivalents) was added, and the reaction was continued. It was checked by an analysis by high performance liquid chromatography using an anion exchange column that the reactants were no longer retained in the column, and after 29 hours from the initiation of reaction, the reaction was terminated. The reaction solution was added dropwise to a mixed solvent of heptane and ethyl acetate, and the mixture was stirred. The mixture was left to stand overnight, and a precipitate thus obtained was collected by filtration and dried under reduced pressure. 35.4 g of crude crystals were obtained.

These crude crystals (34.5 g) were dissolved in DMF (483 mL), and then cation exchange resin DOWEX 50w8 (114 mL) was added thereto. Furthermore, the portion adhered at the time of adding was added in by washing with DMF (35 mL), and the mixture was stirred for 3 hours. The cation exchange resin DOWEX 50w8 was removed by filtration while washing with ethyl acetate, and then the reaction solution thus obtained was added dropwise to a mixed solvent of heptane and ethyl acetate. The mixture was stirred. The mixture was left to stand overnight, and a precipitate thus obtained was collected by filtration and dried under reduced pressure. 33.1 g of block copolymer 3 was obtained.

Block copolymer 3 was hydrolyzed by the same method as that used in Example 1 and analyzed by reverse phase HPLC. The amount of ester-bonded 4-phenyl-1-butanol was 17.2% (w/w) of PEG-pAsp-Ac-3. The reaction ratio of the ester bonds of 4-phenyl-1-butanol was 86.8%, and the ratio of introduction of 4-phenyl-1-butanol was 53.0% of the carboxyl groups of PEG-pAsp-Ac-3.

Block copolymer 3 was analyzed by anion exchange HPLC under the same conditions as in Example 1, and any peak that indicated retention in the column was not recognized.

A solution of block copolymer 3 was titrated (potential difference titration method) by the same method as in Example 1 with a 0.1 mol/L potassium hydroxide liquid, and the number of carboxyl groups per gram was 0.05 mmol/g. As described above, since the number of carboxyl groups in the case where the proportion of carboxyl group was 0% was 0.1 mmol/g or less, block copolymer 3 did not have any residual carboxyl groups.

For block copolymer 3, the amount of diisopropylurea in block copolymer 3 was calculated by the same method as in Example 1, and the amount of diisopropylurea in block copolymer 3 was 3.8% (w/w).

Example 4

Production of Block Copolymer 4

DMF (1102 mL) was added to 62.0 g of PEG (average molecular weight: 12000)-pAsp (polyaspartic acid; average degree of polymerization: 41.6)-Ac (in the formula (1) R1 represents a methyl group, R2 represents a trimethylene group, R3 represents a methylene group, R4 represents an acetyl group, n is about 272, x is about 10.4, and y is about 31.2; hereinafter, abbreviated to PEG-pAsp-Ac-4) produced by the method described in Patent Document 2, the compound was dissolved at 35° C., and DMAP (18.69 g) and 4-phenyl-1-butanol (15.50 g: 0.103 moles; 0.67 molar equivalents relative to 1 mole of carboxyl groups of PEG-pAsp-Ac-4) were added thereto, and the portion adhered at the time of adding was added in by washing with DMF (61 mL). After it was confirmed that the compounds were dissolved, the reaction solution was adjusted to 25° C., DIPCI (38.62 g:2(x+y) equivalents relative to the carboxyl groups of PEG-pAsp-Ac-4=83.2 equivalents) was added. The portion adhered at the time of adding was added in by washing with DMF (61 mL), and the reaction solution was allowed to react for 22 hours at 25° C. In this case, after 20 hours from the initiation of reaction, the reaction ratio of 4-phenyl-1-butanol became constant. On the other hand, according to an analysis by high performance liquid chromatography using an anion exchange column, the reactants were retained in the column. After 22 hours of the reaction, DIPCI (9.66 g:0.5(x+y) equivalents based on the carboxyl groups of PEG-pAsp-Ac=20.8 equivalents) was added, and the reaction was continued. It was checked by an analysis by anion exchange HPLC that the reactants were no longer retained in the column, and after 25 hours from the initiation of reaction, the reaction was terminated. The reaction solution was added dropwise to a mixed solvent of heptane and ethyl acetate, and the mixture was stirred. The mixture was left to stand overnight, and a precipitate thus obtained was collected by filtration and dried under reduced pressure. 72.9 g of crude crystals was obtained.

These crude crystals (71.5 g) were dissolved in DMF (1001 mL), and then cation exchange resin DOWEX 50w8 (236 mL) was added thereto. Furthermore, the portion adhered at the time of adding was added in by washing with DMF (72 mL), and the mixture was stirred for 3 hours. The cation exchange resin DOWEX 50w8 was removed by filtration while washing with ethyl acetate, and then the reaction solution thus obtained was added dropwise to a mixed solvent of heptane and ethyl acetate. The mixture was stirred. The mixture was left to stand overnight, and a precipitate thus obtained was collected by filtration and dried under reduced pressure. 69.7 g of block copolymer 4 was obtained.

Block copolymer 4 was hydrolyzed by the same method as that used in Example 1 and analyzed by reverse phase HPLC. The amount of ester-bonded 4-phenyl-1-butanol was 16.6% (w/w) of PEG-pAsp-Ac-4. Therefore, the reaction ratio of the ester bonds of 4-phenyl-1-butanol was 81.4%, and the ratio of introduction of 4-phenyl-1-butanol was 54.5% of the carboxyl groups of PEG-pAsp-Ac-4.

Block copolymer 4 was analyzed by anion exchange HPLC under the same conditions as in Example 1, and any peak that indicated retention in the column was not recognized.

A solution of block copolymer 4 was titrated (potential difference titration method) by the same method as in Example 1 with a 0.1 mol/L potassium hydroxide liquid, and the number of carboxyl groups per gram was 0.05 mmol/g. As described above, since the number of carboxyl groups in the case where the proportion of carboxyl group was 0% was 0.1 mmol/g or less, block copolymer 4 did not have any residual carboxyl groups.

For block copolymer 4, the amount of diisopropylurea in block copolymer 4 was calculated by the same method as in Example 1, and the amount of diisopropylurea in block copolymer 4 was 3.3% (w/w).

Comparative Example 1

Production According to Production Method Described in Examples of Patent Document 5

Production of Block Copolymer 5

DMF (70 mL) was added to 3.50 g of PEG (average molecular weight: 12000)-pAsp (polyaspartic acid; average degree of polymerization: 43.2)-Ac (in the formula (2) R1 represents a methyl group, R2 represents a trimethylene group, R3 represents a methylene group, R4 represents an acetyl group, n is about 272, x is about 10.8, and y is about 32.4; hereinafter, abbreviated to PEG-pAsp-Ac-5) produced by the method described in Patent Document 2, the compound was dissolved at 35° C., and DMAP (0.87 g), 4-phenyl-1-butanol (1.34 g: 0.0089 moles; 1.00 molar equivalents relative to 1 mole of carboxyl groups of PEG-pAsp-Ac-5) and DIPCI (1.12 g: 1 equivalent relative to 1 mole of the carboxyl groups of PEG-pAsp-Ac-5) were added thereto, and the mixture was allowed to react for 26 hours at 35° C. This reaction solution was added dropwise to a mixed solvent of diisopropyl ether and ethanol, and a precipitate was collected by filtration and dried under reduced pressure. 3.70 g of crude crystals were obtained. These crude crystals were dissolved in a 50% aqueous solution of acetonitrile, and then the solution was passed through cation exchange resin DOWEX 50w8 (40 mL) and washed with 50% acetonitrile. The eluate was concentrated under reduced pressure and then freeze-dried, and thus 3.72 g of block copolymer 5 was obtained.

The block copolymer was hydrolyzed by the same method as that used in Example 1 and was analyzed by reverse phase HPLC. The amount of ester-bonded 4-phenyl-1-butanol was 15.5% (w/w) of the formula (2). The reaction ratio of the ester bonds of 4-phenyl-1-butanol was 49.0%, and the ratio of introduction of 4-phenyl-1-butanol was 49.0% of the carboxyl groups of PEG-pAsp-Ac-5.

Block copolymer 5 was analyzed by anion exchange HPLC under the same conditions as in Example 1, and a peak was detected at a retention time of 14.3 minutes.

Block copolymer 5 was titrated (potential difference titration method) by the same method as that of Example 1 with a 0.1 mol/L potassium hydroxide liquid, and the calculation result for the number of carboxyl groups per gram was 0.23 mmol/g. As described above, since the number of carboxyl groups in the case where the proportion of carboxyl group was 0 was 0.1 mmol/g or less, it is understood that block copolymer 5 had residual carboxyl groups.

For block copolymer 5, the amount of diisopropylurea in block copolymer 5 was calculated by the same method as in Example 1, and the amount of diisopropylurea was 2.3% (w/w).

Comparative Example 2

Production According to Production Method Described in Examples of Patent Document 6

Production of Block Copolymer 6

DMF (13.0 L) was added to 1.73 kg of PEG (average molecular weight: 12000)-pAsp (polyaspartic acid; average degree of polymerization: 41.0)-Ac (in the formula (2) R1 represents a methyl group, R2 represents a trimethylene group, R3 represents a methylene group, R4 represents an acetyl group, n is about 272, x is about 10.3, and y is about 30.8; hereinafter, abbreviated to PEG-pAsp-Ac-6) produced by the method described in Patent Document 2, the compound was dissolved at 35° C., and DMAP (412 g, incorporated by washing in using DMF: 8.7 L) and 4-phenyl-1-butanol (443 g: 2.95 moles; 0.70 molar equivalents relative to 1 mole of carboxyl groups of PEG-pAsp-Ac-6, incorporated by washing in using DMF: 2.2 L) were added thereto, and the reaction solution was cooled to 22.5° C. DIPCI (532 g: 1 equivalent relative to 1 mole of the carboxyl groups of PEG-pAsp-Ac-6, incorporated by washing in using DMF: 2.2 L) was added thereto, and the mixture was allowed to react for 22 hours at 22.5° C. Ethyl acetate and heptane were added to the reaction solution and stirred, and a precipitate thus obtained was collected by filtration and dried under reduced pressure. 2.08 kg of crude crystals were obtained.

The crude crystals were hydrolyzed by the same method as that used in Example 1 and analyzed by reverse phase HPLC. The amount of ester-bonded 4-phenyl-1-butanol was 17.0% (w/w) of the formula (2). The reaction ratio of the ester bonds of 4-phenyl-1-butanol was 77.0%, and the ratio of introduction of 4-phenyl-1-butanol was 53.9% of the carboxyl groups of PEG-pAsp-Ac-6.

The crude crystals were analyzed by anion exchange HPLC under the same conditions as in Example 1, and a peak was detected at a retention time of 16.9 minutes.

14.6 L of DMF was added to the crude crystals (1.94 kg) obtained as described above to dissolve the crude crystals at 31° C., and DMAP (307 g, incorporated by washing in using DMF: 9.7 L) and DIPCI (491 g: 1 equivalent based on the carboxyl groups of PEG-pAsp-Ac, incorporated by washing in using DMF: 4.9 L) were added thereto, and the mixture was allowed to react for 20 hours at 31° C. Ethyl acetate and heptane were added to the reaction solution and stirred, and a precipitate thus obtained was collected by filtration and dried under reduced pressure. 1.85 kg of crude crystals were obtained. 1.83 kg of these crude crystals were dissolved in DMF (22.0 L), and then cation exchange resin DOWEX 50w8 (6.0 L) was added to the solution. The portion adhered at the time of adding was added in by washing with DMF (5.5 mL), and the mixture was stirred for one hour. The cation exchange resin DOWEX 50w8 was removed by filtration while washing with ethyl acetate (69 L), and then ethyl acetate and heptane were added to the reaction solution thus obtained. The mixture was stirred. A precipitate thus obtained was collected by filtration and dried under reduced pressure. 1.79 kg of block copolymer 6 was obtained.

Block copolymer 6 was hydrolyzed by the same method as that used in Example 1 and analyzed by reverse phase HPLC. The amount of ester-bonded 4-phenyl-1-butanol was 15.8% (w/w) of the formula (2). The ratio of introduction of 4-phenyl-1-butanol became 50% after the reaction of the second stage.

Block copolymer 6 was analyzed by anion exchange HPLC under the same conditions as in Example 1, and any peak that indicated retention in the column was not recognized.

Block copolymer 6 was titrated (potential difference titration method) by the same method as that of Example 1 with a 0.1 mol/L potassium hydroxide liquid, and the number of carboxyl groups per gram was 0.04 mmol/g. As described above, since the number of carboxyl groups in the case where the proportion of carboxyl group was 0% was 0.1 mmol/g or less, it is understood that block copolymer 6 had no residual carboxyl groups.

For block copolymer 6, the amount of diisopropylurea was calculated by the same method as in Example 1, and the amount of diisopropylurea was 3.6% (w/w).

The results for the block copolymers obtained in Examples 1 to 4 and Comparative Examples 1 and 2 are summarized in Table 1.

TABLE 1

|  | Average degree of polymerization of PEG-pAsp-Ac | 4-Phenyl-1-butanol (molar equivalents) | 4-Phenyl-1-butanol content | Retention time in anion exchange HPLC (minutes) | Number of residual carboxyl groups (mmol/g) | Amount of diisopropylurea (%) |
|---|---|---|---|---|---|---|
| Example 1 | 41.6 | 0.67 | 16.3 | Undetected | 0.05 | 3.5 |
| Example 2 | 36.4 | 0.73 | 15.5 | Undetected | 0.05 | 3.0 |
| Example 3 | 46.8 | 0.61 | 17.2 | Undetected | 0.05 | 3.8 |
| Example 4 | 41.6 | 0.67 | 16.6 | Undetected | 0.05 | 3.3 |
| Comparative Example 1 | 43.2 | 1.00 | 15.5 | 14.3 | 0.23 | 2.3 |
| Comparative Example 2 | 41.0 | 0.70 | 15.8 | Undetected | 0.04 | 3.6 |

Remark) The term undetected in anion exchange HPLC means that no retained peak was recognized.

As shown in Table 1, all of the block copolymers exhibited the similar 4-phenyl-1-butanol content. On the other hand, block copolymers 1, 2, 3, 4 and 6 were not retained in the column in the analysis by anion exchange HPLC, and exhibited almost equal numbers of residual carboxyl groups. These results imply that the block copolymers substantially do not have carboxyl groups. In regard to the amount of diisopropylurea, only block copolymer 5 has a smaller content thereof. From the above results, it was found that the block copolymers of the present invention were different from the block copolymer described in Patent Document 5, and were the same as block copolymer 6 described in Patent Document 6.

In the method for producing a block copolymer described in Comparative Example 2, first, since the introduced ratio was adjusted by introducing 4-phenyl-1-butanol in an amount larger than the intended content of 4-phenyl-1-butanol, and cutting down the amount of 4-phenyl-1-butanol by the reaction of the second stage, it is to control two different reactions. Furthermore, in the reaction of the second stage, since regulation of residual carboxyl groups of pAsp is also necessary, the production control is complicated and practically difficult. On the other hand, in the present invention, the 4-phenyl-1-butanol content can be controlled by producing the block copolymer in one reaction. Therefore, it can be seen that the production method according to the present invention is an industrially excellent production method with easy production control of the product, as compared with the production method described in Patent Document 6.

The invention claimed is:

1. A method for producing a block copolymer represented by the following formula (1):

[Chemical Formula 2]

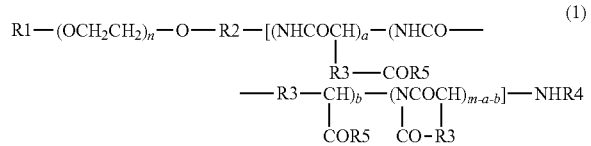

(1)

wherein R1 represents a hydrogen atom or a (C1-C5) alkyl group; R2 represents a (C1-C5) alkylene group; R3 represents a methylene group or an ethylene group; R4 represents a hydrogen atom or a (C1-C4) acyl group; R5 represents (i) a hydroxyl group, (ii) an aryl (C1-C8) alkoxy group optionally substituted with one or more members selected from the group consisting of a methoxy group, an ethoxy group, an isopropoxy group, an n-butoxy group, a t-butoxy group, a fluorine atom, a chlorine atom and a bromine atom, a nitro group, and a cyano group, or (iii) —N(R6)-CO—NHR7 (wherein R6 and R7, which may be identical with or different from each other, each represent a (C3-C6) cyclic alkyl group, or a (C1-C5) alkyl group which may be substituted with a tertiary amino group); n represents 20 to 500; m represents 2 to 200; a represents 0 to 100; b represents 0 to 100, provided that the sum of a and b is greater than or equal to 1 and not greater than m; the proportion of R5 representing a hydroxyl group is 0% to 5% of m; the proportion of R5 representing an aryl (C1-C8) alkoxy group which may have a substituent is 10% to 80% of m; and the proportion of R5 representing —N(R6)-CO—NHR7 is 11% to 30% of m, the method comprising allowing a compound represented by the following formula (2):

[Chemical Formula 1]

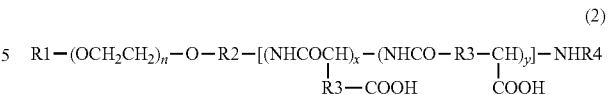

(2)

wherein R1 represents a hydrogen atom or a (C1-C5) alkyl group; R2 represents a (C1-C5) alkylene group; R3 represents a methylene group or an ethylene group; R4 represents a hydrogen atom or a (C1-C4) acyl group; n represents 20 to 500; x represents 0 to 100; and y represents 0 to 100, provided that the sum of x and y is 2 to 200, to react with an aryl (C1-C8) alkyl alcohol which may have a substituent, and a carbodiimide-based compound in an amount of 2(x+y) equivalents or more relative to the amount of carboxyl groups in formula (2) (sum of x and y) in a solvent at 22° C. to 27° C. for 2 hours to 48 hours in a one-pot, one-stage process.

2. The method for producing a block copolymer according to claim 1, wherein R1 represents a methyl group; R2 represents a trimethylene group; R3 represents a methylene group; R4 represents an acetyl group; n is 80 to 400; m is 15 to 60; a is 5 to 60; and b is 5 to 60.

3. The method for producing a block copolymer according to claim 2, wherein the carbodiimide-based compound is diethylcarbodiimide, diisopropylcarbodiimide, dicyclohexylcarbodiimide, or 1-ethyl-3-(3-dimethylaminopropyl)carbodiimide or an inorganic acid salt thereof.

4. The method for producing a block copolymer according to claim 3, wherein the carbodiimide-based compound is diisopropylcarbodiimide.

5. The method for producing a block copolymer according to claim 2, wherein the carbodiimide-based compound is diisopropylcarbodiimide.

6. The method for producing a block copolymer according to claim 1, wherein the carbodiimide-based compound is diethylcarbodiimide, diisopropylcarbodiimide, dicyclohexylcarbodiimide, or 1-ethyl-3-(3-dimethylaminopropyl)carbodiimide or an inorganic acid salt thereof.

7. The method for producing a block copolymer according to claim 6, wherein the carbodiimide-based compound is diisopropylcarbodiimide.

8. The method for producing a block copolymer according to claim 1, wherein the carbodiimide-based compound is diisopropylcarbodiimide.

* * * * *